(12) United States Patent
Sander

(10) Patent No.: US 7,967,441 B2
(45) Date of Patent: Jun. 28, 2011

(54) METHOD FOR ILLUMINATING AN OBJECT, AND A SURGICAL MICROSCOPE HAVING AN ILLUMINATING DEVICE

(75) Inventor: Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 12/729,153

(22) Filed: Mar. 22, 2010

(65) Prior Publication Data

US 2010/0253912 A1    Oct. 7, 2010

(30) Foreign Application Priority Data

Apr. 1, 2009   (DE) .................. 10 2009 002 104

(51) Int. Cl.
*A61B 3/10* (2006.01)
*A61B 3/00* (2006.01)
*G02B 21/00* (2006.01)

(52) U.S. Cl. .................. 351/221; 351/246; 359/368

(58) Field of Classification Search .......... 351/200–246; 359/368–384, 431
See application file for complete search history.

(56) References Cited

U.S. PATENT DOCUMENTS

| 4,715,704 | A | | 12/1987 | Biber et al. | |
| 5,861,982 | A | * | 1/1999 | Takahama et al. | 359/381 |
| 5,898,518 | A | * | 4/1999 | Biber | 359/385 |
| 6,914,721 | B2 | * | 7/2005 | Deverin et al. | 359/388 |
| 7,206,127 | B2 | | 4/2007 | Sander | |
| 7,845,798 | B2 | * | 12/2010 | Kuebler et al. | 351/221 |
| 2004/0120032 | A1 | | 6/2004 | Sander | |
| 2004/0227989 | A1 | | 11/2004 | Obrebski et al. | |
| 2005/0047172 | A1 | | 3/2005 | Sander | |
| 2006/0087729 | A1 | | 4/2006 | Oelckers et al. | |

FOREIGN PATENT DOCUMENTS

| DE | 102 55 960 | 6/2004 |
| DE | 103 39 618 | 3/2005 |
| DE | 103 41 285 | 3/2005 |
| DE | 103 41 521 | 3/2005 |
| DE | 10341 285 | 3/2005 |
| DE | 10 2005 011 121 | 5/2006 |
| DE | 10 2005 055 058 | 5/2007 |
| DE | 10 2006 022 073 | 11/2007 |

* cited by examiner

*Primary Examiner* — Mohammed Hasan
(74) *Attorney, Agent, or Firm* — Alexander R. Schlee; Schlee IP International, P.C.

(57) ABSTRACT

A microscope and a method for illuminating an object to be imaged by a microscope are described. The method includes illuminating the object by primary light of a first spectral intensity distribution and by secondary light of a second spectral intensity distribution, the secondary light arising from the scattering of the primary light; measuring the intensity of at least one wavelength of the secondary light; comparing at least one of the measured intensity and a value derived from this measured intensity to a threshold value; and generating a signal indicating a change in the spectral intensity distribution of the secondary light by indicating whether the at least one of the measured intensity and value derived from this measured intensity either exceed or stay below the predefined threshold value.

19 Claims, 2 Drawing Sheets

METHOD FOR ILLUMINATING AN OBJECT, AND A SURGICAL MICROSCOPE HAVING AN ILLUMINATING DEVICE

CROSS-REFERENCE TO RELATED APPLICATION

This application claims the priority of the German patent application DE 102009002104.3 having a filing date of Apr. 1, 2009. The entire content of this prior German patent application DE 102009002104.3 is herewith incorporated by reference.

BACKGROUND OF THE INVENTION

The present invention relates to a method for illuminating an object to be imaged by a microscope, in particular, a surgical microscope, where the object is illuminated by primary light of a first spectral intensity distribution, as well as by secondary light of a second spectral intensity distribution, the secondary light arising from the scattering of the primary light. The present invention also relates to a surgical microscope having an illuminating device for producing primary light for illuminating an object to be imaged.

Without limiting universality, the following explanations regarding the present invention relate to the special case of what is generally referred to as "red reflex" illumination in the context of surgical microscopes for ophthalmology, where light reflected from the retina is used for surgical purposes. Since the light reflected at the retina has intensity maxima in the red spectral region, one speaks of what is generally referred to as "red reflex." In this application, the object to be examined (the anterior chamber of the eye from the lens to the cornea) is illuminated by primary light of a first spectral light intensity distribution. Light reflected from the retina of the eye is backscattered or reflected towards the object and thus illuminates the object from below, quasi as background or retroillumination. When considered strictly in physical terms, the primary light is not reflected at the retina, but is backscattered there with a solid angle-dependent intensity profile. For the sake of simplicity, the terms "scattering" and "reflection" are to be treated synonymously in the context of the present application, particularly for the application case discussed here.

In cataract surgery, in particular, where the natural lens of the human eye is replaced by an artificial lens, the "red reflex" is utilized to readily detect, under the red retroillumination, any material (bits of tissue) remaining following removal of the natural lens, and to easily remove the same. The "red reflex" is all the more pronounced, the smaller the illumination angles are, the assumption being that the illumination beam path extends through the main objective of the surgical microscope, and that the axis of the main objective is to be considered as the reference axis. Illumination angles in the range of between −2° and +2° promise a is good "red reflex" illumination.

In addition to the application cases described here, the present invention is also generally applicable to the field of microscopy, to the extent that an object is illuminated by primary and secondary light, the secondary light arising from the scattering or reflection of the primary light.

Because the illumination angles used in ophthalmology in the context of the "red reflex" illumination are small and, due to the latest developments, becoming increasingly smaller (to the point of a true 0° illumination), it is becoming increasingly more likely that a patient's eye movement will cause his/her macula to be irradiated directly and dangerously for an extended period of time. The macula (also referred to as "yellow spot") is the region of the human retina having the greatest density of visual cells, and it contains the site of the highest acuity vision. It is imperative to prevent direct irradiation of the macula and any significant endangerment to the eye of the patient resulting therefrom. It is self-evident that a prolonged irradiation of the retina should also be altogether avoided, particularly in view of thermal and phototoxic effects.

In this field, the surgical microscope OPMI Lumera T from Zeiss is known from the related art. The corresponding 2007 prospectus of Carl Zeiss Surgical GmbH, page 4, discusses the "red reflex," which has a bright and stable appearance when the microscope is positioned over the eye of the patient and the illuminating device is switched on. In fact, however, a yellow "red reflex" is discernible in the corresponding image, possibly suggesting that the macula is illuminated.

The technical specifications pertaining to the mentioned product of Carl Zeiss Surgical GmbH are described in the U.S. Patent Application 2004/0227989 A1. It discusses a surgical microscope for ophthalmology where the illumination is directed through the main objective of the microscope. The illuminating device is essentially composed of an optical fiber (fiber illumination), a downstream collimator, as well as of a reflecting mirror, which directs the light that is bundled and collimated by the collimator through the main objective of the microscope into the object plane. The object plane extends through the anterior portion of the eye. A second reflecting mirror configured closer to the observation channels of the stereo microscope directs a portion of the illumination light at an angle of between −2° and +2° relative to the main observation beam paths through the main objective to the object plane, this light being used to produce the "red reflex." This illumination beam is scattered at the retina and reflected back with a solid angle-dependent profile, so that a red retroillumination of the object plane is obtained. Since the mentioned design does not allow the "red reflex" to be maintained at a sufficient intensity level, particularly in the case of movement of the eye, the cited document provides for an illumination ring composed of LEDs (light-emitting diodes) to be placed around the observation channels defined by the zoom systems of the surgical microscope. Each LED emits light in the red spectral region that is nearly completely reflected or scattered back by the retina, so that the eye is protected from thermal stress. In another specific embodiment, a conventional illuminating device is used where an LCD (liquid crystal display) array is configured downstream of the collimator and a white light source. In a central region, the LCD array transmits only red light, while, in an outer annular region, it transmits white light. An inner red illumination cone is thereby formed that is surrounded by an outer white illumination cone. Thus, in accordance with this document, the protective measures are limited to an irradiation of the retina using a suitable (red) spectral region in order to protect the same from thermal damage.

U.S. Pat. No. 6,914,721 B2 of the Applicant, which relates to the same field, describes using a prism combination to deflect the illumination beam path into two different regions of the main objective of the microscope, in order to obtain an oblique and a 0° illumination of the eye to be examined. The oblique illumination is used in this case for the actual object illumination, while the 0° illumination is used for producing the "red reflex." As a protective measure, a shifting mechanism is provided which removes the prism combination from the optical axis of the main objective in a direction perpendicularly to this optical axis. In the shifted state, two oblique illumination beams are generated so that no "red reflex" can occur. The prism combination is moved away from the centered position (with "red reflex") into the shifted position (without "red reflex") as a function of the operating distance and/or as a function of the luminous intensity, in order to protect the retina of the patient's eye.

Consequently, in accordance with the teaching of this document, if a predefined operating distance is fallen short of, or if a predefined illuminating light intensity is exceeded, then, as a protective measure, the "red reflex" is completely prevented by shifting the prism combination.

The U.S. Pat. No. 4,715,704 likewise relates to an ophthalmoscopic surgical microscope, where, to protect the retina of the eye from too high of a radiation load, a retina-protection field stop is provided which is introducible into the illuminating device at a location that is conjugate to the object plane, which, in turn, resides in the anterior portion of the eye (for example, in the cornea). By introducing the field stop for protecting the retina, a central vignetting is achieved, the diameter of the unlighted portion corresponding to the diameter of the pupil of the eye. This protects the retina from further irradiation.

None of the documents mentioned discusses the problem of preventing illumination of the macula during an illumination of the retina.

In another context, the German Patent Application DE 103 41 521 A1 describes a method for determining an object illumination that is adapted to an object under observation, namely for the purpose of enhancing the contrast between healthy and malignant tissue during a microscopic examination. The assumption here is that malignant tissue exhibits a different scattering behavior in the visible spectral region than does healthy tissue. In accordance with the teaching of this document, that wavelength region is ascertained by spectral analysis in which the scattering behavior differences are most visible. The subsequent object examination then takes place using the illumination in the ascertained wavelength region.

Similarly, the German Patent Application DE 103 41 285 A1 describes a surgical microscope which has a spectrometer system that is supplied with scattered illumination light from an operative area in order to spectrally analyze this illumination light. The type of tissue (healthy or malignant) present in the examined operative area can be inferred from the spectral composition of the scattered illumination light. To this end, the operative area is, so to speak, scanned by tiltable deflector elements.

SUMMARY OF THE INVENTION

An object of the present invention, in particular, in the discussed application case of surgical microscopes for ophthalmology, is to effectively protect the macula in the context of the "red reflex" illumination; more generally, to protect or shadow selected regions from where secondary light arises from the object illumination by primary light.

This objective is achieved in accordance with a first aspect of the present invention by a method for illuminating an object to be imaged by a microscope comprising illuminating the object by primary light of a first spectral intensity distribution; illuminating the object by secondary light of a second spectral intensity distribution, the secondary light arising from the scattering of the primary light; measuring the intensity of at least one wavelength of the secondary light; comparing at least one of the measured intensity and a value derived from this measured intensity to a threshold value; and generating a signal indicating a change in the spectral intensity distribution of the secondary light by indicating whether the at least one of the measured intensity and value derived from this measured intensity either exceed or stay below the predefined threshold value.

According to second aspect of the invention, the method according to the present invention comprises: illuminating a first region of the object with the primary light of the first spectral intensity distribution to generate the secondary light of the second spectral intensity distribution; generating by means of a second region of the object another secondary light of a third spectral intensity distribution that differs from the second spectral intensity distribution; measuring the intensity of at least one wavelength of the another secondary light; comparing at least one of the measured intensity and a value derived from this measured intensity of the another secondary light to a threshold value; and activating a protective mechanism to protect the second region from further illumination when the at least one of the measured intensity and a value derived from this measured intensity of the another secondary light exceeds a threshold value. According to this second aspect of the invention, the generation of the another secondary light of a third spectral intensity distribution may take place inadvertently by scattered or reflected light from the first region, or by inadvertent direct illumination of the second region beyond a possibly intended intensity that is necessary for imaging, and the protective mechanism serves to stop or limit this illumination below an acceptable threshold value. The second region is typically the macula of an eye that is more sensitive to high intensity light, while the first region is typically the retina of an eye that is less sensitive to light than the macula.

To implement this method in a practical application, a surgical microscope according to the present invention is used that comprises: an illuminating device for producing primary light for illuminating an object to be imaged with this primary light and illuminating said object with secondary light arising from scattering of the primary light; a measuring device for measuring the light intensity of the secondary light at least one wavelength; an evaluation device for analyzing the measured light intensity by comparing it to a threshold value in a threshold value comparison; and a signaling device generating a signal due to the result of said threshold value comparison, said signal indicating a change in the spectral intensity distribution of the secondary light.

DETAILED DESCRIPTION OF THE INVENTION

In accordance with the present invention, the intensity of the secondary light, which arises from the scattering of the primary light used for direct object illumination, is measured in terms of at least one wavelength (or one wavelength region), and, in response to this measured intensity (or a quantity derived therefrom) exceeding (or falling short of) a predefined threshold value, a signal is generated signaling a change in the spectral intensity distribution of the secondary light and thus a change in that region from where the secondary light is generated by scattering. Whether it is detected that the intensity exceeds or falls short of the threshold value depends on the position of the measured wavelength (or of the wavelength region) in the spectral region of the secondary light originating from a desired region. For example, if the measured wavelength resides in the main spectral region (thus, in a high-intensity spectral region) of the secondary light originating from a desired region (not to be protected) (in other words, the red wavelength is detected in the case of a desired "red reflex"), then a falling short of a predefined threshold value may indicate that the main spectral region of the secondary light, and thus the illuminated region from which this light originates, has shifted. Alternatively, if a wavelength is detected that may be assigned to secondary light from an undesired region (to be protected) (in the present case, yellow light, for example), then an exceedance of a predefined threshold value may indicate that precisely this undesired region is illuminated at this point.

The mentioned change in the region that is illuminated by primary light, from which secondary light is produced by scattering, may be induced, on the one hand, by movement in this region or, however, by a change in the direction of the illumination. In the case of the "red reflex" illumination discussed above in the context of surgical microscopes for ophthalmology, such changes occur, in particular, in response to movements of the eye. For example, a rolling of the eye may cause the macula to be struck by rays (illuminated). In such a case, instead of a "red reflex," a "yellow reflex" appears (which will also be referred to as such in the following). Associated therewith is a change in the spectral composition of the light that is reflected back into the object plane due to scattering. In accordance with the present invention, this change is detected by measuring the intensity of the secondary light at least one wavelength, for which two methods are suited: On the one hand, that wavelength may be considered at which intensity maxima (in the red spectral region) normally occur (for example, in the case of the retina illumination). If a change in the spatial region from where the secondary light arises induces a change in the spectral composition (for example, in the case of illumination of the macula instead of the remaining region of the retina), then this fact may be detected in that, at the selected wavelength (in the red spectral region), the intensity falls short of a predefined threshold value. On the other hand, the wavelength to be measured may also be set to be within a wavelength region where the region to be protected, from which the secondary light arises, has an intensity maximum (in the present example, in the yellow spectral region). In the case of a transition to a region of this kind, the intensity of the light would then exceed a predefined threshold value at the selected wavelength (in the yellow spectral region). In both of the cases mentioned, a signal is generated in accordance with the present invention that signals a change in the spectral intensity distribution of the secondary light and thus an undesired transition from a region that is not to be protected to a region that is to be protected, from where the secondary light arises.

In the case of the above described intensity measurement in the yellow spectral region, the method according to the present invention may also be used to ascertain an (age-related) macular degeneration. The xanthophyll, which is ophthalmoscopically visible as macular yellow, is a pigment that is absorbent in the blue spectral region, is composed of the carotenoids, lutein and zeaxanthin, and is contained in the photoreceptors. Xanthophyll protects the macula, on the one hand, by absorbing short-wave high-energy radiation and, on the other hand, by its ability to bind free radicals. Therefore, a small concentration of xanthophyll in the macula may be considered as a possible risk factor for the disease of age-related macular degeneration (AMD) (in this regard, compare also M. Hammer, D. Schweitzer, L. Leistritz: "Bestimmung der Konzentrationsverteilung des Makulapigmentes aus Reflexions- und Fluoreszenzaufnahmen" [English: Determining the Concentration Distribution of the Macular Pigment from Reflection and Fluorescence Images], "Ophthalmologe" [English: The Ophthalmologist] 2003, vol. 100; pp. 611-617). Therefore, at the moment when an intensity measurement is performed in the yellow spectral region of the macular yellow in accordance with the method of the present invention, the measured intensity value may be compared to that of a healthy macula. If the measured intensity value is lower than that corresponding to a healthy macula, then a macular degeneration may be inferred herefrom. Consequently, in this case, the measured intensity in the yellow spectral region of the macular yellow falling short of a predefined threshold value would generate a signal which signals a change, in this case caused by a pathological macular degeneration, of the spectral intensity distribution of the secondary light. Moreover, in this case, however, the method according to the present invention may be further used to protect the macula (that has changed due to disease), in that an exceedance of another threshold value, which, at this point, is predefined as a function of the lower intensity of the macular reflection, indicates an illumination of the (degeneratively diseased) macula.

A surgical microscope according to the present invention having an illuminating device for producing primary light for illuminating an object to be imaged, which is also illuminated by secondary light arising from scattering of the primary light, is characterized by a measuring device for measuring the light intensity in terms of at least one wavelength (or one wavelength region) of the secondary light arising from scattering of the primary light, in addition, by an evaluation device for analyzing the measured light intensity using a threshold value comparison; as a function of the result of this comparison, it being possible for a signal to be generated that signals a change in the spectral intensity distribution of the secondary light.

A surgical microscope of this kind may be used as a device for detecting macular degeneration. For further clarification in this regard, reference is made to the above explanations in connection with the method according to the present invention. The precondition for this use is that the mentioned measuring device measure a light intensity in the yellow spectrum of the macular yellow; that a (first) threshold value be defined in terms of the healthy macula; and that, in response to falling short of this (first) threshold value, a signal be generated indicating a possible (age-related) macular degeneration.

Independently of or in addition to this described application, the surgical microscope according to the present invention may also be used to protect an illuminated region. For that purpose, the surgical microscope according to the present invention has a protective device for activating a protection mechanism for illuminated regions as a function of the mentioned signal, respectively the presence of such a signal.

If an already degeneratively diseased macula is to be protected from illumination, then it is self-evident that the threshold value to be selected is to be set correspondingly lower than in the case of a healthy macula. An exceedance of the (lower) threshold value may then serve as an indication that the (diseased) macula is illuminated, thereby leading to the activation of the protective mechanism in question.

A method according to the present invention may be implemented very effectively by employing a surgical microscope of this kind. For example, in response to the evaluation device generating the mentioned signal, the protective device may be driven to activate a protective mechanism. Thus, by generating the mentioned signal, effective measures may be taken to prevent an undesired irradiation of a region (to be protected), from where secondary radiation is produced by the scattering of light used for object illumination.

In the following, embodiments of the method according to the present invention, as well as of the surgical microscope according to the present invention are collectively explained. Thus, embodiments of the method described in the dependent claims may be reflected in corresponding embodiments of the surgical microscope and vice versa. It is also noted that the features of the present invention may be used not only in the combination described herein and in the following, but also in other combinations and—where appropriate—also alone. Thus, features described in combination with one another may also be used separately from one another for the present invention.

It is particularly advantageous for white light to be used as primary light, thus for a white light source to be used for generating primary light in the illuminating device. A white light illumination of the object to be imaged by a microscope is more favorable for the color neutrality of the image under observation, as well as for the user's ability to discern details, than is the illumination of an object using a specific wavelength, as described, for instance, in the U.S. Patent Application 2004/0227989 A1 for protecting the retina, as discussed in the introductory part of this Specification.

Since the secondary light arises from the scattering of the primary light (apart from the special physical cases which do not play a role in ophthalmologic applications), the spectrum of the secondary light is generally contained in the spectrum of the primary light. It is advantageous when the spectral intensity distribution of the primary light is selected to have a wider bandwidth than that of the secondary light, in particular to cover more colors in the visible spectral region. Particularly beneficial is the use of white light, as already mentioned.

As previously mentioned, the present invention is advantageously applied in cases where the anterior portion of the eye, in particular, the posterior portion of the capsular bag, is used as the object to be imaged. Light reflected or backscattered from the retina of the eye is then used as secondary light. As is likewise already mentioned, to measure intensity, it is advantageous to use one wavelength or one wavelength region either in the red or the yellow spectral region. In this case, in accordance with the present invention, the transition from the retina to the macula is signaled by the intensity exceeding a predefined threshold value in the yellow spectral region, or by the measured intensity falling short of a predefined threshold value in the red spectral region.

In the application case in question, measuring the light intensity entails, in particular, measuring the intensity of the yellow and/or of the red reflected light. A sensor suited for this purpose having a filter with an appropriate bandwidth suffices in the simplest case. On the other hand, a spectrometer or a color temperature meter may also be used for this purpose. Using these devices, a spectral analysis may be performed, which, however, is technically more complex and more expensive than using a sensor with a filter.

In principle, the regions from where secondary light arises may also be discriminated in that—still in the context of the already described application case—the spectral intensity distribution of the "red reflex" is initially recorded and properly stored, whereupon the spectral intensity distribution of the secondary light is recorded—preferably continuously—during the microscopic examination. A differential spectrum of the stored and of the (continuously) recorded spectrum first yields significant deviations from zero (thus, differential maxima) when the macula is struck (by light), thus, when instead of a "red reflex," a "yellow reflex" is obtained. Thus, in this case, the intensity of the secondary light is (continuously) measured over a wavelength region which includes the yellow spectral region, and, if the differential spectrum derived therefrom exceeds a predefined threshold value in the yellow spectral region, the mentioned signal is generated, which signals a change in the characteristics of the illuminated region and thus may activate suitable protective mechanisms. Depending on the characteristics of the intensity distributions in the regions of interest, one skilled in the art will perform a suitable discrimination. If the differences in the spectral intensity distributions are great enough, as in the case of the retina and macula under consideration here, then the simple case may apply whereby the intensity is measured in terms of one wavelength (or in a narrow wavelength region) and is then (directly) compared to a threshold value.

The present invention makes it possible to exclude specific regions, which produce "ambient radiation" in the sense mentioned above, from the illumination or to protect them from an excessively high illumination intensity. To this end, a protective mechanism is expediently provided, which may be activated as a function of the result of the threshold value comparison described above.

Accordingly, the present method, which provides for illuminating a first region with primary light of a first spectral intensity distribution to produce secondary light of a second spectral intensity distribution, may be used to protect a second region which produces secondary light of a third spectral intensity distribution that is different from the second spectral intensity distribution. In this case, the signal produced by a threshold value comparison is used to activate a protective mechanism to protect the second region in question from further illumination. Preferably, in the case of the second and third spectral intensity distribution of the secondary light, different intensity maxima are present, and (at least) one such intensity maximum (respectively, the assigned wavelength) is used for measuring intensity in accordance with the method described above.

As already explained above, it is advantageous to use an intensity maximum of the third spectral intensity distribution of the secondary light from the second region to be protected to measure intensity (for example, of the yellow wavelength of the macula); in response to an exceedance of a predefined threshold value, the signal for activating a protective mechanism being generated. Conversely, it may be advantageous to use an intensity maximum of the second spectral intensity distribution of the secondary light from the first region to measure intensity (for example, of the red wavelength from the remaining retina); in response to a falling short of a predefined threshold value, the signal for activating a protective mechanism then being generated.

One or more of the events named in the following may be used as protective mechanisms: Actuating a field stop or a protective filter, adjusting lenses and/or prisms or deflector elements, the mentioned optical elements being configured in the propagation direction of the primary light or, when the optical element is actuated accordingly, being configurable in the propagation direction of the primary light. In detail: A field stop at a location in the illuminating device that is conjugate to the object plane may be swung into the primary illumination beam path, as described, for example, in the U.S. Pat. No. 4,715,704 discussed in the introductory part of the Specification. Instead of a field stop, a protective filter may be provided, which filters that light out of the primary light which is absorbed in the undesired region (for example, macula) and may cause thermal and/or phototoxic damage there. Thus, to protect the macula, a protective filter would be used which is opaque (nontransparent) to light outside of the yellow wavelength region. Electro-optical changes in illumination may also be used for this purpose. By adjusting lenses or prisms, in particular, reflecting prisms or, more generally, deflector elements within the illuminating device that are configured in the propagation direction of the primary light, the primary illumination beam path may be varied in its direction, so that the illumination angle required for a "red reflex" is no longer maintained. In this manner, the scattering of the primary light may be altogether prevented, so that, at the same time, an illumination of the undesired region (macula) is prevented.

On the other hand, the mentioned protective mechanism may include one or more measures from a group that is formed by reducing the intensity of the primary light and by generating an acoustic and/or visual signal, in particular for data superimposition into the field of view. By reducing the intensity of the primary light, the illumination of the undesired region (for example, the macula) may be reduced to a harmless level. Acoustic and/or visual signals indicate to the user (for example, the surgeon) that he/she is illuminating the undesired region (macula), thereby allowing the user himself/herself to initiate appropriate remedial measures. In surgical microscopes, a superimposition of data is useful whereby, for example, a visual warning signal is provided in the field of view of the surgeon.

The present invention is clarified in greater detail in the following with reference to the accompanying drawings, along with descriptions detailing the advantages and embodiments thereof.

DETAILED DESCRIPTION OF THE DRAWINGS

Figure 1:
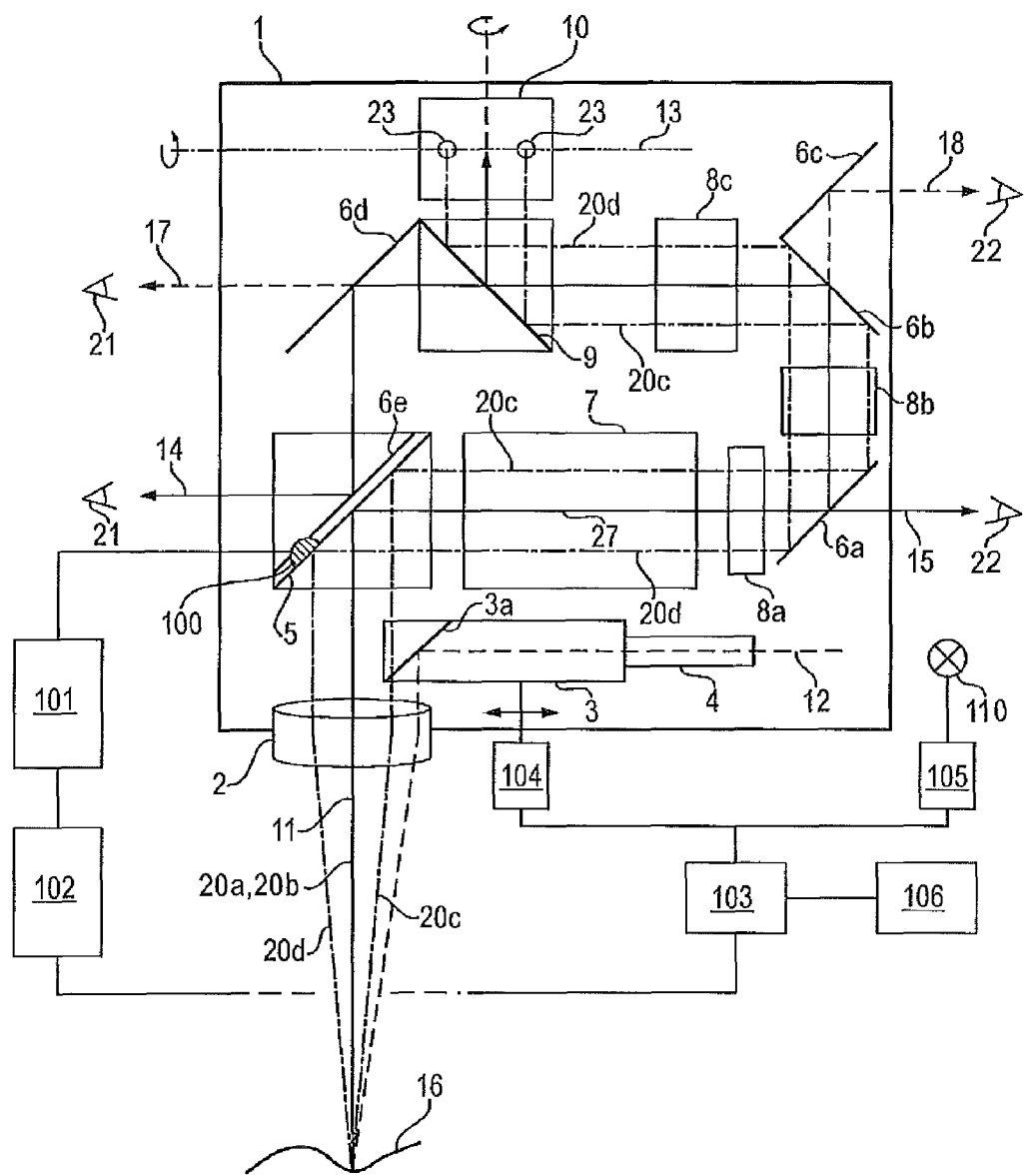
FIG. 1 is a schematic representation of a surgical microscope that is suited for the present invention.

FIG. 1 schematically depicts a stereo microscope, as is suited, in particular, for ophthalmology. The design and principle of operation of such a stereomicroscope are described in detail in the German Patent Application DE 102 55 960 A1 and in the corresponding U.S. Pat. No. 7,206,127 B2. These descriptions are hereby expressly incorporated herein by reference in their entirety. To avoid repetitive explanations and to facilitate understanding, only the important aspects of the illustrated stereomicroscope, as well as the points that are relevant to the present invention are described in detail in the following.

As essential optical components, stereomicroscope 1 has a main objective 2, a horizontal zoom system 7, and an ocular system (not shown). A first deflector element 5 is provided between main objective 2 and zoom system 7. Behind zoom system 7, additional deflector elements 6a, 6b, 6c, 6d, 6e, 9, 10, as well as optical add-on components 8a, 8b, 8c are provided. This design employing a horizontal zoom system 7 permits a low overall height, which is a decisive advantage for surgical microscopes, in particular (for example, for use in ophthalmology).

Illuminating device 3 directs light provided by a fiber cable 4 via a deflector element 3a onto object 16 to be observed; in this case, illumination beam path being directed through main objective 2. The main axis of illuminating device 3 is denoted by 12.

In the illustrated case, zoom system 7 has two observation channels each for the main observer, as well as for the assistant. Accordingly, main objective 2 has two main observation beams 20a, 20b, as well as two assistant observation beams 20c, 20d passing through it in the vertical direction, which, after being deflected by deflector element 5, enter into the corresponding observation channels of zoom system 7. 27 denotes the central axis of zoom system 7.

The mentioned observation beams are then deflected vertically or horizontally by the mentioned additional deflector elements 6a through 6e, it being possible for some of the mentioned deflector elements to be designed as beam splitters, whereby the observation axes denoted by 15, 18 and 17 may be realized. The important observation axes are denoted by 14 and 23 in FIG. 1 and are used for main observer 21, respectively assistant observer 22. For the sake of clarity, the binocular tubes, including the eyepieces needed for the observation, are not shown in FIG. 1.

Beams 20a through 20d, which are deflected into the horizontal direction by deflector element 6b, strike deflector element 9, which is configured to merely deflect beams 20c, 20d onto assistant observation axis 23, while beams 20a, 20b pass by deflector element 9 unimpeded and strike additional deflector element 6d. From there, via deflector elements 6e, beams 20a, 20b reach observation axis 14 for main observer 21. Observation axis 14 features an especially small vertical spacing to object 16 to be observed.

In one particular specific embodiment, deflector element 10 is rotatable about axis 31 and may additionally or alternatively be pivotable about axis 13. With regard to this and further embodiments of the stereomicroscope presented here, reference is again expressly made to the publications mentioned at the outset.

In FIG. 1, 11 denotes the axis of symmetry of main objective 2; in the case of the mentioned optical add-on components, 8a through 8c, it may be a question of filters, laser shutters, optical splitters, data superimposition devices or the like. In addition, diaphragms, displays and the like come into consideration. Suitable and customary add-on components are known to one skilled in the art.

Surgical microscope 1 shown in FIG. 1, that is particularly suited for ophthalmology, may be used for surgical purposes on the eye utilizing what is commonly referred to as the "red reflex" illumination, as explained in detail in the introductory part of the Specification. To protect the macula of the eye from harmful illumination or also to be able to diagnose degenerative macular diseases, surgical microscope 1 is to be advantageously refined and modified as follows:

A sensor 100, configured here in the periphery of deflector element 5, including a filter suited for the wavelength to be measured, along with a downstream device 101 used for signal analysis, is used here as a measuring device for measuring the light intensity in terms of at least one wavelength. In the case of object 16 to be imaged and illuminated, it is a question, in particular, of the posterior portion of the capsular bag of the eye. The primary light emitted by illuminating device 3 is reflected or backscattered as secondary light by the retina of the eye. This secondary light produces, so to speak, an additional illumination of object 16 from below. An additional illumination in the red wavelength region is desired, while an illumination in the yellow wavelength region indicates that the macula of the eye, which is to be protected from illumination, is struck (by light).

As already repeatedly explained, in the present application case, a wavelength (or a wavelength region) may be measured in the yellow or red spectral region. The sensor signal processed by signal analysis unit 101 is fed to a downstream unit for signal processing, i.e., evaluation device 102. In this case, the measured spectral light intensity is analyzed using a threshold value comparison; as a function of the result of this comparison, it being possible for a signal to be generated.

If, for example, measurements are taken in the yellow wavelength region, i.e., in the region from about 560 to 590 nm, then a relatively low reflectance should result, as long as the retina of the eye is illuminated. In the case of an (unintentional) illumination of the macula, the intensity of the reflected light would rise abruptly in the yellow spectral region. Thus, by properly defining a threshold value, a change in the illumination of the retina relative to the macula may be detected when the measured light intensity exceeds the threshold value. In response to the outputting of a signal by evaluation device 102 to a control unit 103, measures are taken to protect the illuminated macula.

In the illustrated exemplary embodiment, the protective device comprises mentioned control unit 103, as well as a control unit 104, and a light-source regulation/control 105 as protective mechanisms. Control unit 104 may, for example, adjust prisms and/or lenses in illuminating device 3 and/or actuate filters and/or shutters in order to reduce the intensity of the primary light, respectively, modify the frequency of the primary light in such a way that the illumination of the macula does not have any damaging effect. Additionally or alternatively, a light-source control 105 may be provided as a protective mechanism that is likewise driven by control unit 103. Light-source control 105 acts on light source 110 and decreases the supply voltage of light source 110 to the point where the intensity of the primary light is reduced to a value that is harmless to the macula.

It is expedient to provide, in parallel, an external protective signal device 106, which, in addition to the mentioned protective mechanisms, outputs visual and or acoustic signals to signal that the region of the macula to be protected has been struck (by light).

Figure 2:
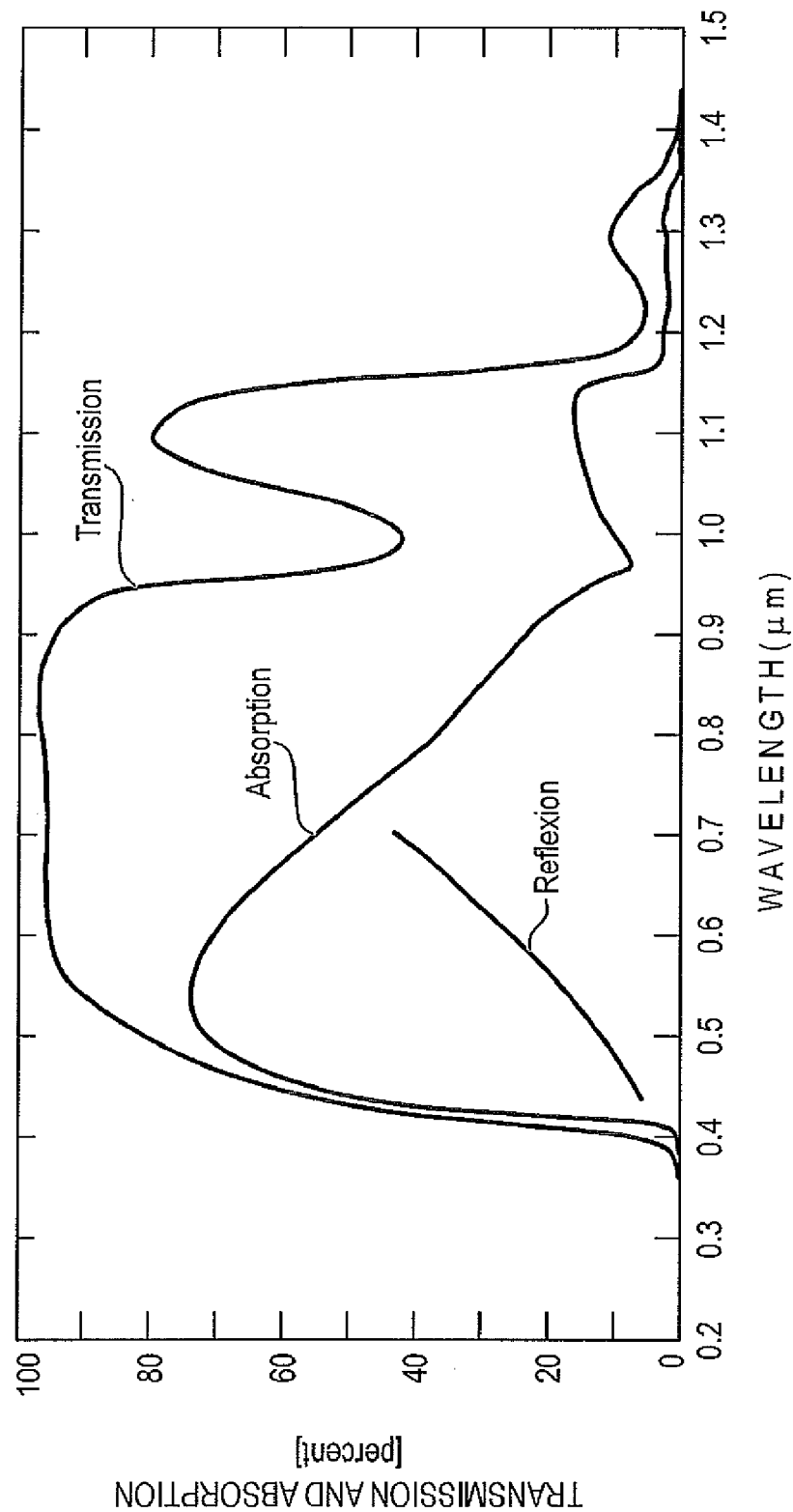
FIG. 2 shows transmission, absorption and reflection curves for the "red reflex" of the retina of a human eye.

In a schematic view, FIG. 2 shows a transmission curve of the body of the eye to the retina and an absorption curve for the retina, plotted in percentage values ("percent") over a wavelength region ("wavelength") of 0.2 to 1.5 µm. It is apparent herefrom that the maximum absorption occurs in the blue to green spectral region. In the orange to red wavelength region and beyond, there is a high transmittance. The description is taken from the book "Safety with Lasers and Other Optical Sources," by David Sliney and Myron Wolbarsht, Plenum Press, 1980, p. 89. A reflection curve is sketched in this description. The reflection increases continuously from the blue, over the green, yellow and orange spectral region until the red spectral region is reached. This is due to what is generally referred to as the "red reflex." On the other hand, the maximum reflectivity of the macula is in the yellow wavelength region of between 560 and 590 nm.

LIST OF REFERENCE NUMERALS 1 stereo microscope, surgical microscope
2 main objective
3 illuminating device
3a deflector element
4 fiber cable
5 deflector element
6a-6e deflector element
7 zoom system
8a-8c optical add-on components
9 deflector element
10 deflector element
11 axis of symmetry of the main objective
12 main axis
13 axis of rotation
14, 15, 18, 17, 23 observation axes
16 object
20a, 20b main observation beam
20c, 20d assistant observation beam
21 main observer
22 assistant observer
27 central axis of the zoom system
31 axis of rotation
100 sensor
101 signal analysis unit
102 signal processing unit, evaluation device
103 control unit
104 control unit for adjusting prisms/lenses or for actuating filters/shutters
105 light-source regulation/control
106 external protective signal device
110 light source

What is claimed is:

1. A method for illuminating an object to be imaged by a microscope, comprising:
    illuminating a first region of the object by primary light of a first spectral intensity distribution to generate secondary light of the second spectral intensity distribution;
    illuminating the object by secondary light of a second spectral intensity distribution, the secondary light arising from the scattering of the primary light;
    generating by means of a second region of the object another secondary light of a third spectral intensity distribution that differs from the second spectral intensity distribution;
    measuring the intensity of at least one wavelength of the another secondary light;
    comparing at least one of the measured intensity and a value derived from this measured intensity of the another secondary light to a threshold value; and
    activating a protective mechanism to protect the second region from further illumination when the at least one of the measured intensity and a value derived from this measured intensity of the another secondary light exceeds a threshold value.

2. The method as recited in claim 1, comprising using white light as the primary light.

3. The method as recited in claim 1, comprising using a posterior portion of the capsular bag of an eye as the object.

4. The method as recited in claim 3, comprising using one of light reflected and light backscattered from a retina of the eye as secondary light.

5. The method as recited in claim 1, comprising measuring the intensity of at least one wavelength of the secondary light using at least one of a wavelength and a wavelength region in a red spectral region for measuring intensity.

6. The method as recited in claim 5, comprising using for measuring intensity such wavelengths of the second and third spectral intensity distributions of the secondary light where these spectral intensity distributions comprise intensity maxima, wherein these wavelengths used of the second and third spectral intensity distributions differ from each other.

7. The use as recited in claim 6, comprising:
    using an intensity maximum of the third spectral intensity distribution of the another secondary light from the second region to be protected to measure intensity;
    generating a signal when the intensity maximum of the third spectral intensity distribution of the another secondary light exceeds a predefined threshold value; and
    activating by this generated signal the protective mechanism.

8. The method as recited in claim 6, comprising:
    using an intensity maximum of the second spectral intensity distribution of the secondary light from the first region to measure intensity;

generating a signal when the intensity maximum of the second spectral intensity distribution of the secondary light stays below a predefined threshold value; and activating by this generated signal a protective mechanism.

9. The method as recited in claim 1, comprising using at least one of a wavelength and a wavelength region of the another secondary light in the yellow spectral region for measuring intensity.

10. The method as recited in claim 1, comprising using a sensor having a filter for measuring the intensity.

11. The method as recited in claim 1, comprising performing a spectral analysis for measuring intensity.

12. The method as recited in claim 1, comprising:

selecting the protective mechanism from a group of optical elements consisting of: a field stop, a shutter, a protective filter, adjusting lenses, adjusting prisms, and deflector elements;

actuating a selected one of the protective mechanisms; and placing the selected one of the protective mechanisms in a beam path of the primary light.

13. The method as recited in claim 1, comprising selecting as the protective mechanism at least one of reducing the intensity of the primary light and generating at least one of an acoustic and visual signal.

14. The method as recited in claim 1, comprising using as the second region to be protected the macula of an eye and as the first region the remaining retina.

15. A surgical microscope comprising:

an illuminating device for producing primary light for illuminating an object to be imaged with this primary light and illuminating said object with secondary light arising from scattering of the primary light;

a measuring device for measuring the light intensity of the secondary light at at least one wavelength;

an evaluation device for analyzing the measured light intensity by comparing it to a threshold value in a threshold value comparison;

a signaling device generating a signal due to the result of said threshold value comparison, said signal indicating a change in the spectral intensity distribution of the secondary light; and a protective device for activating a protective mechanism for illuminated regions as a function of the signal.

16. The surgical microscope as recited in claim 15, wherein the protective mechanism comprises a control unit for performing at least one of the actions consisting of: adjusting lenses, adjusting prisms, actuating a protective filter and actuating a shutter.

17. The surgical microscope as recited in claim 15, wherein the protective device comprises at least one of a light-source regulation and a control.

18. The surgical microscope as recited in claim 15, wherein the protective mechanism comprises a protective signal device for generating at least one of an acoustic and a visual signal.

19. The surgical microscope as recited in claim 15, wherein the measuring device for measuring the light intensity includes a sensor for detecting the light intensity and an upstream filter for selecting the wavelength to be measured.

\* \* \* \* \*